US009864889B2

(12) United States Patent
Tonnelier (10) Patent No.: US 9,864,889 B2
(45) Date of Patent: Jan. 9, 2018

(54) AUTHENTICITY TAG AND METHODS OF ENCODING AND VERIFICATION

(71) Applicant: MOBILEAD, Paris (FR)

(72) Inventor: Laurent Tonnelier, Paris (FR)

(73) Assignee: MOBILEAD, Paris (FR)

( * ) Notice: Subject to any disclaimer, the term of this patent is extended or adjusted under 35 U.S.C. 154(b) by 0 days.

(21) Appl. No.: 15/274,262

(22) Filed: Sep. 23, 2016

(65) Prior Publication Data

US 2017/0091504 A1 Mar. 30, 2017

(30) Foreign Application Priority Data

Sep. 28, 2015 (EP) .................................. 15306512

(51) Int. Cl.
*G06K 7/10* (2006.01)
*G06K 7/14* (2006.01)
(Continued)

(52) U.S. Cl.
CPC ......... *G06K 7/1417* (2013.01); *G06K 7/1413* (2013.01); *G09C 5/00* (2013.01); *H04L 9/3226* (2013.01); *H04L 2209/34* (2013.01)

(58) Field of Classification Search
CPC ........................... G06K 7/1413; G06K 7/1417
(Continued)

(56) References Cited

U.S. PATENT DOCUMENTS 7,124,953 B2 * 10/2006 Anttila ..................... G06K 1/18
235/462.45

9,010,622 B2 * 4/2015 Kim .................. G06F 17/30879
235/375
(Continued)

FOREIGN PATENT DOCUMENTS

FR 3008211 A1 1/2015
FR 3009409 A1 2/2015
(Continued)

OTHER PUBLICATIONS

European Search Report for 15306512.3, dated Apr. 28, 2016.

*Primary Examiner* — Seung Lee
(74) *Attorney, Agent, or Firm* — Meagher Emanuel Laks Goldberg & Liao, LLP (57) ABSTRACT

An object is associated with an identifier which is detectable on the object. The identifier may be an inherent characteristic of the object itself or its packaging, or it may reflect a random or arbitrary value which may then be disposed on the object or its packaging deliberately in a readable form for the purposes of the invention. Additionally, there is disposed a machine readable code comprising a URI incorporating a representation of the object identifier encoded according to one of a number of predefined encoding methods (algorithm and associated parameters), and an encoding identifier, specifying the encoding method used. A reader can read the machine readable code, decode it according to specified encoding method, and prepare a representation of it for comparison with the characteristic reflecting the object identifier. The machine readable code and the characteristic reflecting the object identifier may be readable for example by optical, tactile, radio, olfactive or acoustic mechanisms. The URI may additionally be defined to call a local resource adapted to process the code. The URI may additionally be defined to specify a web site.

17 Claims, 7 Drawing Sheets

(51) Int. Cl.
*G09C 5/00* (2006.01)
*H04L 9/32* (2006.01)

(58) Field of Classification Search
USPC .............................. 235/462.01, 462.15, 494
See application file for complete search history.

(56) References Cited

U.S. PATENT DOCUMENTS

| | | | |
|---|---|---|---|
| 2008/0245870 A1* | 10/2008 | Lee ................... | G06F 17/30879 |
| | | | 235/462.01 |
| 2010/0304852 A1 | 12/2010 | Szrek et al. | |
| 2011/0154052 A1 | 6/2011 | Yang et al. | |
| 2012/0089518 A1* | 4/2012 | Blonchek ............... | G06Q 10/10 |
| | | | 705/50 |
| 2013/0091002 A1 | 4/2013 | Christie | |

FOREIGN PATENT DOCUMENTS

| | | |
|---|---|---|
| WO | 2008/028804 A2 | 3/2008 |
| WO | 2013/048459 A1 | 4/2013 |

\* cited by examiner

AUTHENTICITY TAG AND METHODS OF ENCODING AND VERIFICATION

FIELD OF THE INVENTION

Authenticity tag and methods of encoding and verification

BACKGROUND OF THE INVENTION

Logistics as a field inherently attracts information technology solutions, and as internet technology has developed through the twentieth century a number of different mechanisms for making a connection between any physical object and an electronic information handling system have been developed. Punched cards were developed as the original input means for computing devices, and the possibility of using similar cards was quickly identified as a rapid means of registering the sale of an object. A major development in this field came with the development of the Universal Product Code (UPC) system, based on the reading of a one or two dimensional barcode with a laser scanner. On the basis of this and related technologies, virtually all packaged consumer goods today are provided with such a code. More recently, matrix, or two dimensional bar codes, such as "QR Codes" (registered trade mark in some jurisdictions) described in U.S. Pat. No. 5,726,435 have become common. Such codes are able to encode more information in a small area than conventional 1 dimensional bar codes, and as such are frequently used to encode a Uniform Resource Indicator (URI) for example as defined in IETF Request For Comments RFC 1630. Meanwhile, in addition to these optical solutions, radio based tagging solutions such as those based on RFid tags are increasingly widespread.

One frequent usability issue with machine readable codes of this kind is that the machine readable code is often not comprehensible to a human reader. It is therefore common to accompany the machine readable code with a human readable representation of the key content of the machine readable code.

While in the context of the tagging of commercial goods there is little incentive to use misleading or corrupts tags, as such tags become common in a wide range of situations outside the strictly regulated field of commerce, such misuse becomes more likely. This is compounded by the increasing capabilities of modern tagging systems. For example, the capacity for QR codes or RFID tags to incorporate a URI which may point to an internet site hosting dangerous code, or even to incorporated harmful scripting itself means that these technologies may become a threat. Meanwhile, the fact that QR tags may appear on posters, business cards, letters and so on means that the context in which such codes are used is increasingly uncontrolled.

Accordingly, it is desirable to provide a mechanism whereby the content of a machine readable code may be verified with regard to the object with which it is associated.

Certain partial solutions to this problem are known.

Each NFC Chipset memory has a unique serial number, called the UID (Unique Identifier). It may be 7 bytes long (7×8=56 bits, 04:73:91:A2:16:3C:81) or 4 bytes long (4×8=32 bits, like 04:73:91:A2).

On some NFC Chipsets a specific feature allows a so called «UID ASCII mirror for automatic serialization of NDEF messages". Writing a URL (ex http://xt.ag/#) in an NFC tag for example in the form UID: 04:73:91:A2:16:3C: 81 gives an extended URL stored in the NFC Chipset memory. This feature writes the UID in ASCII hex format in the NDEF URL. This may support some server side verification concerning the registered usage of the chip in question.

Meanwhile, an extension to the standard QR Code format has been developed entitled: "Security QR Code (SQRC)". The terms "Security QR Code" and "SQRC" are registered trademarks in some jurisdictions. SQRC contains both encrypted and normally readable data. While these features can be used to combat fraud and help prevent counterfeit, grey-market and black-market issues, this approach remains dependant either on the reader device being pre-programmed with the encryption algorithm and parameters of the code to be decoded (and no others), or being in communication with a remote server which is able to provide the required information.

FR3008211 describes a method for printing security graphics on a support that is to be secured, characterized in that it involves using, in combination, at least three different types of printing security graphics taken from a group of eligible printing security graphics items, and in that said printing security graphics items that are used are interdependent by construction, such that a modification to one of the EGS items forming the print item automatically results in an identifiable inconsistency.

FR3009409 concerns a method for encoding an access to a computer resource, consisting of including, in a physical representation of the code, a first item of information encoded according to a first encoding type corresponding to the access path and to the identification of said computer resource, and capable of being decoded by a reader, characterised in that: the physical representation further comprises an item of validity condition information encoded according to a second encoding type, corresponding to a validity condition of the access to said computer resource,— said validity condition information being capable of being decoded by an application installed on an element of the network including the reader of the physical representation, one or a plurality of gateways and the server that hosts said computer resource. Where this system operates at a purely local level, it relies on a predefined encryption key whereby security is reinforced with reference to additional validity information entered by a user or from an additional machine readable code. It is desirable to provide an approach offering satisfactory security without recourse to these additional steps. It is desirable to provide a tagging solution offering security and improved flexibility.

SUMMARY OF THE INVENTION

In accordance with a first aspect there is provided an object associated with a object identifier and having a readable characteristic reflecting the object identifier and bearing a machine readable code, wherein the machine readable code comprises a URI having a hierarchical portion incorporating a representation of the object identifier encoded according to a selected one of a plurality of predefined combinations of encoding algorithms and parameters, each combination having a respective encoding identifier, and wherein the hierarchical portion of the URI further specifies the encoding identifier corresponding to the combination of algorithm and parameters used to encode said object identifier.

This approach provides a secure mechanism for authenticating an object and its identifier, without the need for recourse to network communications and remote databases.

The use of a URI makes implementations flexible and accessible via well known standards and compatible platforms.

According to a development of the first aspect, the scheme name portion of the URI is selected so as to cause the URI to be interpreted as a call to a local resource adapted to de-code said object identifier.

Adapting the URI in this way provides a mechanism for calling the local resource in a manner which is platform independent and requires minimal modification of existing platforms.

According to a further development of the first aspect, the URI is defined so as to resolve to a web site.

Web sites are a convenient mechanism for conveying information to a user. This may be a mechanism for reporting the results of the decoding, or as a channel for conveying ancillary information in parallel.

According to a further development of the first aspect, said readable characteristic reflecting the object identifier is a physical characteristic of the object.

Using a physical characteristic of the object as an identifier can improve security due to the fact that the physical characteristic can be chosen as inherent to the value or function of the object itself, and therefore difficult to modify without also affecting its value or function. This approach may also avert the need for additional steps for disposing an identifier on the object.

According to a further development of the first aspect, the physical characteristic comprises a one or two dimensional image disposed on said object.

One or two dimensional images can be easily disposed on the object by printing etc, and as such offer a convenient manner for modifying the object to improve its uniqueness, and the extent to which it can be uniquely identified and distinguished from similar objects.

According to a further development of the first aspect, the physical characteristic comprises a surface bearing tactile or palpable features.

Certain objects may inherently incorporate tactile or palpable features, while others may easily receive such features. Such features may be more permanent and less easily damaged than printed images, and may be better suited for reading in certain circumstances, such as in the dark, under water or by sight impaired individuals.

According to a second aspect there is provided a method of defining an identification code for an object comprising the steps of:

selecting an object identifier for said object;

deriving a numerical representation of said object identifier;

selecting a combination of encoding algorithm and parameters from a predefined plurality of combinations of encoding algorithm and parameters, each said combination having a respective encoding identifier, encoding said object identifier with said selected combination of encoding algorithm and parameters, defining a URI having a hierarchical portion incorporating said encoded object identifier and the encoding identifier corresponding to the combination of algorithm and parameters used to encode said object identifier; and encoding said URI in a machine readable form.

According to a third aspect there is provided a method of verifying a URI containing an identification code for an object, comprising the steps of reading said URI via a machine reading interface;

extracting an encoding identifier specifying a combination of algorithm and parameters from the URI;

retrieving the combination of algorithm and parameters corresponding to said encoding identifier from a predefined plurality of combinations of encoding algorithm and parameters, each said combination having a respective encoding identifier, decoding a remaining part of said URI using the retrieved combination of algorithm and parameters to obtain a decoded object identifier; and preparing a representation of the decoded object identifier.

According to a development of the third aspect, the method comprises the further steps of reading a characteristic of said object, said characteristic reflecting said object identifier, and comparing said characteristic with said representation of said decoded object identifier.

This approach provides a secure mechanism for authenticating an object and its identifier, without the need for recourse to network communications and remote databases. The use of a URI makes implementations flexible and accessible via well known standards and compatible platforms.

According to a further development of the third aspect the method comprises a further step of extracting the scheme name portion of said URI, and interpreting the contents of the scheme name portion of the URI as a call to a local resource prior to said step of extracting an encoding identifier, wherein the remaining steps of the method are implemented by said resource.

Adapting the URI in this way provides a mechanism for calling the local resource in a manner which is platform independent and requires minimal modification of existing platforms.

According to a further development of the third aspect the method comprises the further step of notifying the result of said verification to a user.

By notifying the user of the results, the loop is closed, enabling the user to assess whether the object and its identifier in fact correspond.

According to a fourth aspect there is provided an apparatus for defining an identification code for an object. Such an apparatus may be adapted to select a combination of an encoding algorithm and associated parameters from a memory containing a plurality of combinations of encoding algorithm and parameters. The memory may further contain a respective encoding identifier associated with each combination. The apparatus may further be adapted to define a URI having a hierarchical portion incorporating an identifier for said object encoded in accordance with said selected combination of algorithm and parameters, where the hierarchical portion further incorporates the encoding identifier corresponding to the selected combination of algorithm and parameters According to a development of the fourth aspect the apparatus may further be adapted to encode the URI in a machine readable form.

According to a fifth aspect there is provided an apparatus for verifying a URI containing an identification code for an object, adapted to extract an encoding identifier specifying a combination of algorithm and parameters from the URI; retrieving the combination of algorithm and parameters corresponding to said encoding identifier from a memory containing a predefined plurality of combinations of encoding algorithm and parameters. The memory further contains a respective encoding identifier associated with each combination. The apparatus may further be adapted to decode a remaining part of the URI using the retrieved combination of algorithm and parameters to obtain a decoded object identifier.

According to a development of the fifth aspect the apparatus may further be adapted to prepare a representation of the decoded object identifier.

According to a further development of the fifth aspect an apparatus may further comprise a reader adapted to read a characteristic of the object reflecting the object identifier, and further be adapted to compare the characteristic with the representation of the decoded object identifier.

According to a sixth aspect there is provided a computer program adapted to implement the steps of the third aspect.

According to a seventh aspect there is provided a computer readable medium incorporating the computer program of the fourth aspect.

BRIEF DESCRIPTION OF THE DRAWINGS

The above and other advantages of the present invention will now be described with reference to the accompanying drawings, in which.

DETAILED DESCRIPTION

Figure 1:
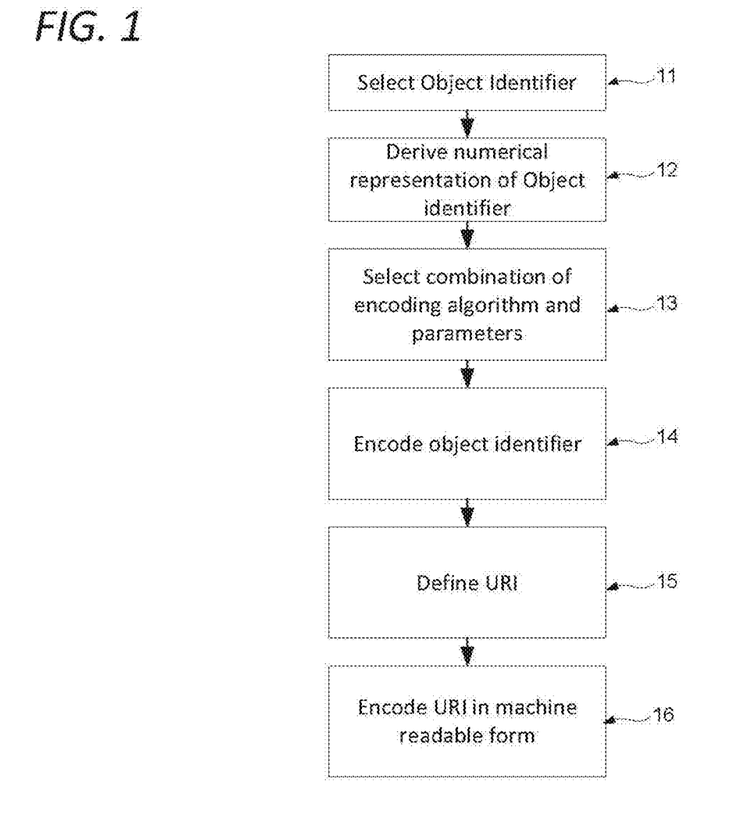
FIG. 1 shows steps of a method of defining an identification code in accordance with a first embodiment.

FIG. 1 shows steps of a method of defining an identification code in accordance with a first embodiment. As shown in FIG. 1, the method starts at a first step 11 selecting an object identifier for an object.

In some cases the object identifier may be a code already associated with the object such as a GTIN, or a serial code or random value, which may be generated specifically for the purposes of the invention, for example using 128 bit UUID v1, UUID v4 generation etc. In other cases the code may be derived from the appearance or some other recognizable characteristic of the object.

Where the code is derived from the appearance of the object itself, this may be any aspect of the object's appearance such a surface coloration, texture, or patterning or any combination of these or other characteristics. These features may also be disposed on the object as an additional step, for example by printing directly onto the object, and may include cardioids, guilloches or fractals, or other shapes suited to distinguishing the object from similar objects, as well as or in addition to alphanumeric codes. Accordingly, one way or another, a readable characteristic is present on the object which reflects the selected object identifier.

The method next proceeds to step 12 at which a numerical representation of the object identifier is derived. In some cases the identifier may be inherently numerical, for example comprising an alphanumeric code or other set of characters that can be defined numerically. Otherwise, this may involve scanning, rasterisation or optical character recognition, or simply processing an existing code to ensure compliance with the format requirements of the embodiment. The method next proceeds to step 13 of selecting a combination of encoding algorithm and parameters. In accordance with this embodiment, there is provided a predefined set of combinations of encoding algorithm and associated parameters each set having a corresponding encoding identifier identifying that set.

These encoding algorithms may be any method, from trivial processes such as incrementing the ASCII value of each character by a particular number, changing the radix, ciphering, encryption, etc. The parameters associated with any algorithm may incorporate an encryption key or any other information required to encode the information. The plurality of combinations may all use the same algorithm, and differ by their associated parameters, or may use a variety of different algorithms. Where a variety of different algorithms are used, these may offer a range of more or less secure options. There may be any number of sets from a few up to a very large number.

Any of these predefined sets may be selected, either at random, as specified by a user or in response to some other consideration, for example on the basis of the content of the object identifier, or any combination of these approaches. Once a set is selected, it is used at step 14 to encoding said object identifier. At step 15 the method then defines a URI whose hierarchical portion incorporates the encoded object identifier generated at step 14, and also the encoding identifier, that is to say, a reference to the combinations of algorithm and parameters used to encode the object identifier.

The method then proceeds to step 16 at which the URI is encoded in a machine readable form.

The machine readable form may take any form. By way of example:

it may be optically readable, for instance in the form of an alphanumeric code, or a one, two (including "QR" codes) or three dimensional bar code, or a holographic code. The machine readable code may be disposed together with other visual content, for example by steganography.

Optical reading, by way of a camera, laser scanner etc, has a security advantage over radio communications in that it requires a line of sight and specified alignment with the object, making covert reading of the object difficult. Consumer devices are very frequently provided with a camera device, meaning that such readers can be implemented without special hardware.

It may be magnetically readable, for example in the form of a magnetic strip.

It may be readable by radio communication, for example by RFID, NFC or Bluetooth Low Energy systems.

Radio communications have the advantage of not requiring physical contact, or even line of sight between the object and a reader. Short range radio communications are increasingly used in consumer devices, meaning that such readers can be implemented without special hardware.

It may be readable acoustically, or as a sound wave emitted by the object, either continuously, periodically or in response to stimulation by a user or generated by the user device implementing the invention. This stimulation may be mechanical, sonic, electronic, optical or by any other suitable mechanism.

Although sound waves do not require physical contact, or even line of sight between the object and a reader, they are subject to diffusion and interference inherently limiting the range at which they can be used. As such, in some implementations sound waves can offer a compromise between the characteristics of optical and radio reading. Consumer devices are often provided with microphones, meaning that such readers can be implemented without special hardware.

It may be readable as a tactile or palpable code, for example in the form of punched indentations or bumps, which may be read by optical or mechanical means.

By way of example, an object identifier "12345" may be considered, in connection with the following library of four encoding combinations:

A: Algorithm: Increment number, Parameter: 5
B: Algorithm: Increment number, Parameter: 1
C: Algorithm: Decrement number, Parameter: 5
D: Algorithm: Decrement number, Parameter: 1

On this basis, if at step 13 set B is selected, the result of step 14 of encoding the object identifier with the selected combination of encoding algorithm and parameters would be "67890", corresponding to each of the digits of the object identifier incremented by 5 in accordance with encoding combination B as defined above.

The URI Defined at step 15 would then take the form "VT:B67890", where "VT" is the scheme part of the URI, and "B67890" is the hierarchical part. VT may correspond to any suitable URI scheme or protocol. This may be an existing protocol, or one specified for the purpose of the present invention. In the case of the present example, it is assumed that a scheme having the "VT" protocol name indicating a Verifiable Tag has been specified for the purpose of the present invention. In accordance with the present embodiment, the URI is defined to comprise a hierarchical portion incorporating said encoded object identifier "B67890" and the encoding identifier corresponding to the combination of algorithm and parameters used to encode said object identifier "B". The encoded object identifier and the encoding identifier corresponding to the combination of algorithm and parameters used to encode said object identifier may be disposed in the hierarchical portion in any order. Although the convention of the URI standard is to refer to this part of the URI as hierarchical portion, this need not suggest any hierarchical relationship between its components in accordance with the present embodiment. In some embodiments, the URI may incorporate further material in addition to the components mentioned in the present embodiment.

Figure 2:
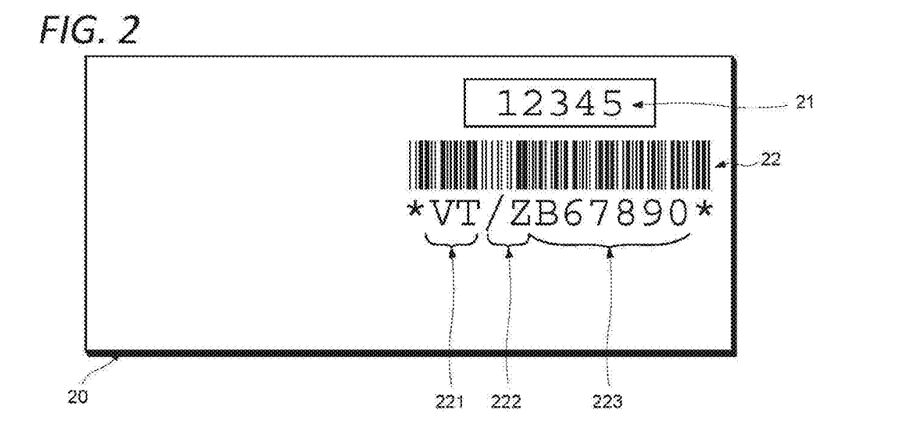
FIG. 2 shows an object marked with a tag in accordance with the embodiment described with regard to FIG. 1.

FIG. 2 shows an object marked with a tag in accordance with the embodiment described with regard to FIG. 1. As shown in FIG. 2, there is provided an object 20. This object may be an article of value such as a piece of consumer electronics, or a carton or container which may have some content, or not, or it may simply be a label to be stuck to some other article in due course. As shown, the object 20 is associated with an object identifier 12345, which is reflected in the readable characteristic 21 which as described above is the printed numeric code "12345". As should be clear from the forgoing this code may be any recognizable pattern or characteristic, however this numeric code is selected for the sake of simplicity.

The object 10 furthermore bears a machine readable code 22. As show, the machine readable code is a one dimensional bar code, encoded here in the three of nine format. In the present example, the machine readable code encodes the text "*VT/ZB67890*". The leading and training asterisks are imposed by the 3 of 9 standard to indicate the start and end of a code, "VT" 221 corresponds to the URI scheme or protocol as previously mentioned, and the sequence "/Z" 222 represents the colon character in extended 3 of 9 coding. Accordingly, any suitable device capable of reading extended 3 of 9 coding would render the machine readable code 22 as "VT:B67890". In accordance with Internet standard STD 66, a URI comprises a scheme name followed by a hierarchical part, separated by a colon. Accordingly, the machine readable code 22 comprises a URI.

In accordance with the method of FIG. 1 and the associated worked example, the object identifier 12345 is encoded to 67890 under encoding combination B, and accordingly by incorporating "B67890" the hierarchical portion 223 incorporates a representation of the object identifier encoded according to a selected one of a plurality of predefined combinations of encoding algorithms and parameters. As noted above with respect to the worked example, each combination of algorithm and parameters has a respective encoding identifier A, B, C or D, and here the hierarchical portion of the URI further specifies the encoding identifier corresponding to the combination of algorithm and parameters used to encode said object identifier, "B".

As mentioned above, the object identifier code may be derived from the appearance of the object itself for example on the basis of any aspect of the object's appearance such a surface coloration, texture, or patterning or any combination of these or other characteristics. According to certain further embodiments, these features may be disposed on the object as an additional step, for example by printing directly onto the object, and may include cardiods, guilloches or fractals, or other shapes suited to distinguishing the object from similar objects.

Still further, the object identifier code may be derived from an olfactive characteristic of said object, in which case the object identifier code may be read by an olfactometer (electronic nose). In certain embodiments, for example those where the object identifier code is derived from an olfactive characteristic of the object, the object itself may be a quantity of liquid, paste or powder. Where this is the case, the machine readable code may be disposed on a vessel containing the object.

Still further, the object identifier code may be derived from a surface bearing tactile or palpable features, for example by a punch code, embossed features, or the like.

Figure 3:
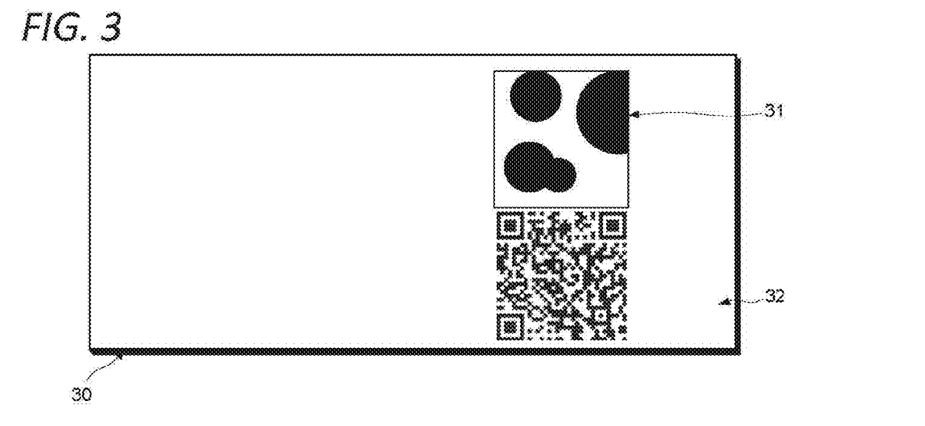
FIG. 3 shows a further object marked with a tag in accordance with the embodiment described with regard to FIG. 1.

FIG. 3 shows a further object marked with a tag in accordance with the embodiment described with regard to FIG. 1. As shown in FIG. 3, the object 30. The object 30 is associated with a readable characteristic 31 which as shown takes the form of an apparently somewhat random pattern of variously sizes black circles in a box. In accordance with a specified encoding process (whose definition is beyond the scope of this description) this pattern represents the object identifier "12345".

The object 30 furthermore bears a machine readable code 32. As show, the machine readable code is a two dimensional bar code in the QR code format, and lacking the human readable rendering of the code, which for the purposes of the present description is assumed to constitute a machine readable code 32 comprising a URI, incorporating a representation of the object identifier encoded according to a selected one of a plurality of predefined combinations of encoding algorithms and parameters, and further specifying the encoding identifier corresponding to the combination of algorithm and parameters used to encode the object identifier.

It will be understood that in the case of the example of FIG. 3, the step 11 of the method described above with regard to FIG. 1 will comprise the creation of the graphical readable object identifier 32, and that this will need to be disposed on the object.

Figure 4:
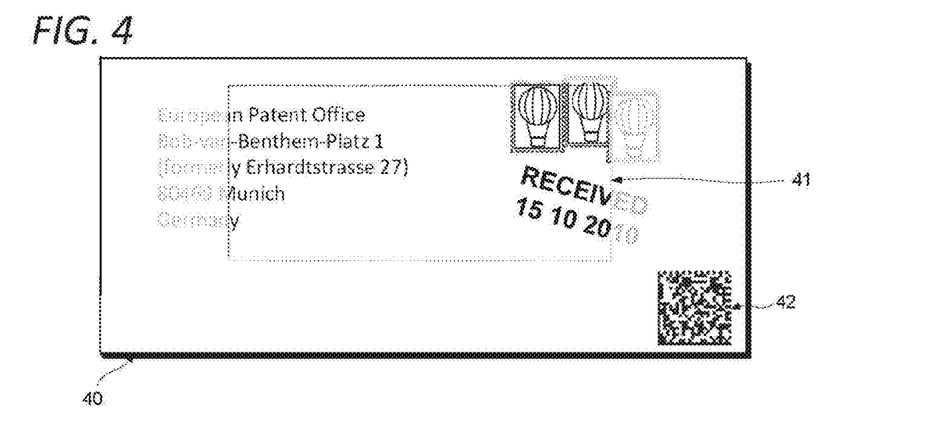
FIG. 4 shows a further object marked with a tag in accordance with the embodiment described with regard to FIG. 1.

FIG. 4 shows a further object marked with a tag in accordance with the embodiment described with regard to FIG. 1. As shown in FIG. 4, the object 40 is associated with a readable characteristic 41 which as shown takes the form of a part of the address, postage stamps and reception rubber stamp disposed within a specified portion of the surface of the object. In accordance with a specified encoding process (whose definition is beyond the scope of this description) this pattern corresponds to the numeric code "12345", which is assigned as the object identifier.

The object 40 furthermore bears a machine readable code 42. As show, the machine readable code is a two dimensional bar code, and lacking the human readable rendering of the code, which for the purposes of the present description is assumed to constitute a machine readable code 42 comprising a URI, incorporating a representation of the object identifier encoded according to a selected one of a plurality of predefined combinations of encoding algorithms and parameters, and further specifying the encoding identifier corresponding to the combination of algorithm and parameters used to encode the object identifier.

It will be understood that in the case of the example of FIG. 4, the step 11 of the method described above with regard to FIG. 1 will comprise the selection of the portion of the surface of the object, and step 12 will comprise scanning or otherwise digitizing this portion.

While FIGS. 2, 3 and 4 present particular combinations of respective types of readable characteristic reflecting an object identifier with a particular type of machine readable code, it will be appreciated that other embodiments are envisaged comprising any suitable readable characteristic including any of the types suggested in this description, any suitable object identifier, including any of the types suggested in this description, with any suitable machine readable code, including any of the types suggested in this description, without restriction.

Figure 5:
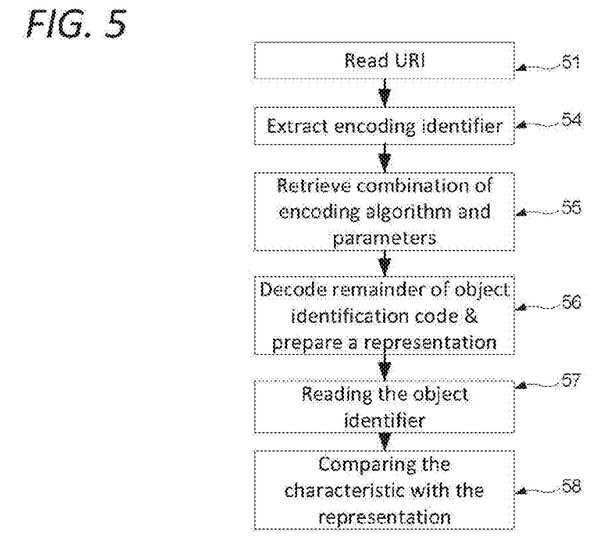
FIG. 5 shows the steps of a method of verifying an object identifier in accordance with an embodiment.

FIG. 5 shows the steps of a method of verifying an object identifier in accordance with an embodiment. As shown in FIG. 5, the method starts at step 51, at which machine readable code containing a URI incorporating an object identification code is read from an object. As described above, this may involve optical, magnetic, radio, sonic or other machine interfaces adapted to read the URI. As described above, the object identifier may have been arbitrarily associated with the object, or may have been derived from some characteristic of the object. The retrieved URI is then processed at step 54 to extract the encoding identifier specifying the combination of algorithm and parameters used to encode the object identifier. The combination of algorithm and parameters corresponding to the encoding identifier extracted from the Object identifier code is retrieved at step 55, and then used at step 56 to decode a remaining part of the object identifier code using the combination of algorithm and parameters to retrieved at step 55 obtain a decoded object identifier, on the basis of which a representation is prepared. This representation may be in a form suitable for human review for example as a graphical representation for example along the lines of element 21 of FIG. 2 or 31 of FIG. 3, or for machine processing as for example a digest of the a scanned version of element 41 of FIG. 4, as described above or otherwise. A representation of the decoded object identifier is prepared. The representation is prepared in such a way that the representation and the characteristic of the object representing the object identifier will be identical, or similar to a degree exceeding a predetermined threshold, where the characteristic is unchanged and the machine readable code is decoded using the proper algorithm and parameters. In cases where the characteristic is determined and disposed on the object from a predetermined identifier, the representation may be generated by repeating the same process. In cases where the characteristic is an inherent property of the object, the representation may in some cases be prepared by reversing the process originally used to obtain the object identifier from the characteristic.

In accordance with certain variants, the method may proceed to step 57 at which the characteristic (21, 31, 41) reflecting the object identifier on the object is read, and compared at step 58 to the representation of the decoded object identifier obtained at step 56.

It will be appreciated that certain steps can be implemented in different orders without departing from the invention, for example the object identifier can be read (step 57) from the object at any stage of the process.

The step of reading the object identifier will depend on the nature of the identifier itself—as discussed above, alphanumeric or printed graphical identifiers may be read by an optical scanner, as may many characteristics of the appearance of the object itself. Reading three-dimensional characteristics such as surface textures, blemishes, punch codes or superposed layers such as the postage stamps of FIG. 4 and the like may require laser scanning or other such techniques. Olfactive characteristics may be read by an olfactometer (electronic nose), and so on. The step of reading will generally produce a numeric (for example, digital or binary) representation of the object identifier. In some cases it may be possible to compare this directly with the decoded object identifier, in other cases the read code may require some normalization or pre-processing to ensure that it is suitable for comparison. For example, where the object identifier is derived from a visible characteristic of the object itself, additional processing may be required to ensure that the requisite part of the objects surface has been extracted, that the numerical representation has the proper orientation, that any variations due to ambient lighting have been corrected, etc.

The comparison of the read object identifier with the decoded object identifier may require that the two versions of the identifier (representation and characteristic) be identical, in particular where the read object identifier is in the form of an alphanumeric code printed on the object. In other cases, the comparison may allow for some degree of variation, e.g. by specifying a required similarity threshold. Still further, the comparison may be carried out on an impressionistic basis, whereby an assessment is made whether or not the two identifiers give a general impression of identity.

An impression based comparison may be carried out by a user, in which case the representation of the object identifier may be presented to the user by the system implementing the method, and receive the user's indication as to whether the two are considered to match.

A variety of software tools are available for the comparison operation, for example the OpenCV library.

Where the representation of the object identifier is presented to the user by the system implementing the method, it may be necessary to regenerate a graphical representation of the object identifier from the numerical form in which it is handled by the system implementing the method for presentation to the user.

Using a URI for the encoding of the object identifier provides a flexible, ubiquitous platform for encoding and interpretation. Encoding the identifier provides security and supports proof of data integrity and origin. By identifying the encoding in the URI itself the autonomy of the identification system is improved, since more information is available locally.

Figure 6:
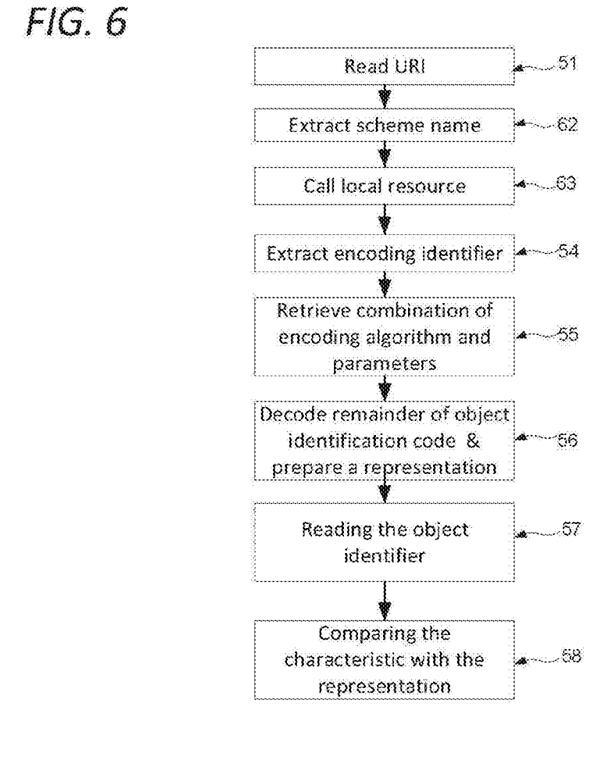
FIG. 6 shows the steps of a method of verifying an object identifier in accordance with a further embodiment.

FIG. 6 shows the steps of a method of verifying an object identifier in accordance with a further embodiment. The method of FIG. 6 is similar to that of FIG. 5, but comprises the further step 62 after step 51 and preceding step 54. According to this embodiment, at step 62 the scheme name is extracted from the URI constituting the object identification code, and then interpreted at step 63 to call a local resource wherein the remaining steps of the method are implemented by that resource.

The scheme name may be any suitable existing URI protocol or scheme name, or may be a scheme name specified for the purposes of the present invention. Typically, device operating systems or other platform software will be configured to handle URIs according to various schemes or protocols, and handle each according to its characteristics and requirements. Suitable configuration of such software can enable such devices to properly interpret any scheme adopted for implementation of the present invention.

The identification of the encoding in the URI itself supports the possibility of locally decoding the object identifier. Known systems are obliged to communicate with remote systems for the identification, decoding and verification of identifiers, whilst in accordance with the present invention these activities can be implemented locally. This means that systems implementing the invention need not have network access.

It is an advantage of this embodiment that verification can take place purely locally. The algorithms and associated parameters can all be stored in the device which is used in the verification process. The library of algorithms and associated parameters may be static, or updated regularly, for example when network connectivity is available. The possibility of regularly updating the library improves the security of the solution.

In some embodiments, the URI may optionally be defined so as to resolve to a remote network location or web site, as well as or instead of calling a local resource. The remote network location may implement some aspects of the verification process. Calling a website in this manner may also provide a mechanism allowing for a graceful handling of situations where the local device is unable to decode the object identifier for any reason. Calling a website in this manner may provide also provide a mechanism for the handling of failed verifications, either as a mechanism for notifying the user of the implications of the failed verification, or as a mechanism for reporting the failed verification to a remote server for monitoring or auditing purposes. Calling a website in this manner may further provide a mechanism for presenting ancillary information to a user in parallel with the verification process.

According to a further development of the methods described with reference to FIG. 5 or 6, the method may comprising the further step of notifying the result of said verification to a user. This may be performed by any convenient mechanism, for example by displaying a message of a display unit of the user device implementing the method, emitting a sound, etc.

According to certain embodiments, an object is associated with an identifier which is detectable on the object. The identifier may be an inherent characteristic of the object itself or its packaging, or it may reflect a random or arbitrary value which may then be disposed on the object or its packaging deliberately in a readable form for the purposes of the invention. Additionally, there is disposed a machine readable code comprising a URI incorporating a representation of the object identifier encoded according to one of a number of predefined encoding methods (algorithm and associated parameters), and an encoding identifier, specifying the encoding method used. A reader can read the machine readable code, decode it according to specified encoding method, and prepare a representation of it for comparison with the characteristic reflecting the object identifier. The machine readable code and the characteristic reflecting the object identifier may be readable for example by optical, tactile, radio, olfactive or acoustic mechanisms. The URI may additionally be defined to call a local resource adapted to process the code. The URI may additionally be defined to specify a web site.

It will be appreciated that the forgoing embodiments are merely non-limiting examples. In particular, the various forms the object might take (a product in the form of a solid article, a powder, paste or liquid, or the container for any of these), the nature of the object identifier (the appearance, olfactive characteristic etc, whether inherent to the object or imposed as part of the inventive process), the type of machine readable code (bar code, rfid tag, etc.) may be used together in any combination.

The disclosed methods can take form of an entirely hardware embodiment (e.g. FPGA), an entirely software embodiment (for example to control a system according to the invention) or an embodiment containing both hardware and software elements. Software embodiments include but are not limited to firmware, resident software, microcode, etc. The invention can take the form of a computer program product accessible from a computer-usable or computer-readable medium providing program code for use by or in connection with a computer or an instruction execution system. A computer-usable or computer-readable can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

In some embodiments, the methods and processes described herein may be implemented in whole or part by a user device. These methods and processes may be implemented by computer-application programs or services, an application-programming interface (API), a library, and/or other computer-program product, or any combination of such entities.

The user device may be a mobile device such as a smart phone or tablet, a computer or any other device with processing capability, such as a robot or other connected device.

Figure 7:
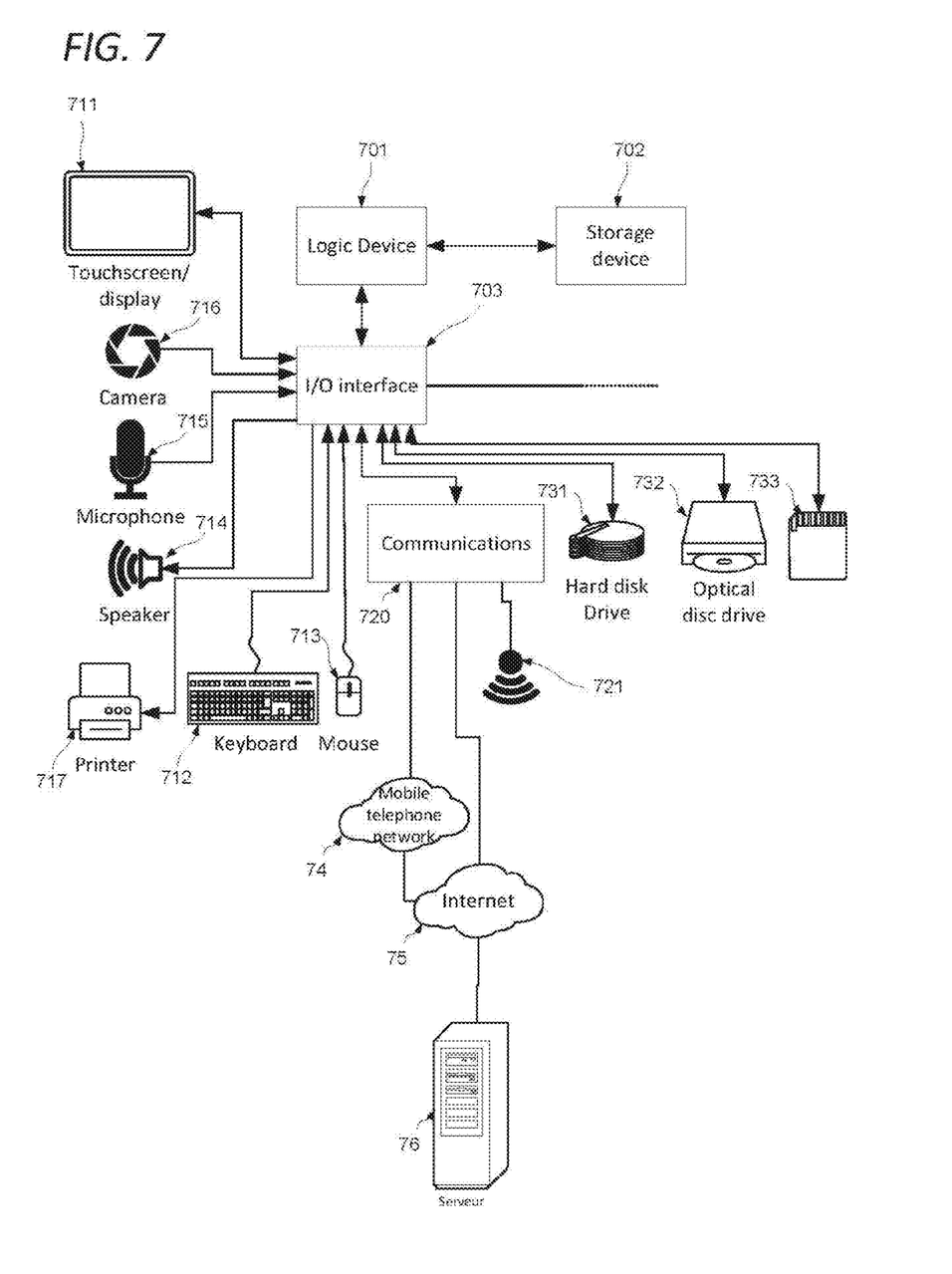
FIG. 7 shows a generic computing system suitable for implementation of embodiments of the invention.

FIG. 7 shows a generic computing system suitable for implementation of embodiments of the invention.

A shown in FIG. 7, a system includes a logic device 701 and a storage device 702. The system may optionally include a display subsystem 711, input subsystem 712, 713, 714, communication subsystem 720, and/or other components not shown.

Logic device 701 includes one or more physical devices configured to execute instructions. For example, the logic device 701 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 701 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 701 optionally may be distributed among two or more separate devices, which may be remotely located and/or configured for coordinated processing. Aspects of the logic device 701 may be virtualized and executed by remotely accessible, networked computing devices configured in a cloud-computing configuration.

Storage device 702 includes one or more physical devices configured to hold instructions executable by the logic device to implement the methods and processes described herein. When such methods and processes are implemented, the state of storage 702 device may be transformed—e.g., to hold different data.

Storage device 702 may include removable and/or built-in devices. Storage device 702 may comprise one or more types of storage device including optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device may include volatile, nonvolatile, dynamic, static, read/write, read-only, random-access, sequential-access, location-addressable, file-addressable, and/or content-addressable devices.

In certain arrangements, the system may comprise an interface 703 adapted to support communications between the Logic device 701 and further system components. For example, additional system components may comprise removable and/or built-in extended storage devices. Extended storage devices may comprise one or more types of storage device including optical memory 732 (e.g., CD, DVD, HD-DVD, Blu-Ray Disc, etc.), semiconductor memory 733 (e.g., RAM, EPROM, EEPROM, FLASH etc.), and/or magnetic memory 731 (e.g., hard-disk drive, floppy-disk drive, tape drive, MRAM, etc.), among others. Such extended storage device may include volatile, nonvolatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 701 and storage device 702 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

In particular, the system of FIG. 7 may be used to implement embodiments of the invention.

For example a program implementing the steps described with respect to FIG. 1 may be stored in storage device 702 and executed by logic device 701. The library of algorithms and parameters may be stored in storage device 702 or the extended storage devices 732, 733 or 731. The Logic device may cause the camera 716 or Near Field interface 721 to read the object identifier from the object, or otherwise cause the printer 717 or Near Field interface 721 to impose the object identifier and/or the machine readable code on the object.

Similarly a program implementing the steps described with respect to FIG. 5 or 6 may be stored in storage device 702 and executed by logic device 701. The library of algorithms and parameters may be stored in storage device 702 or the extended storage devices 732, 733 or 731. The Logic device may cause the camera 716 or Near Field interface 721 to read the machine readable code from the object to obtain the URI. The Logic device may then extract encoding identifier from the uri, and retrieve the specified combination of algorithm and parameters on the basis of this encoding identifier. The Logic device may then, in accordance with the program, decode a remaining part of said URI using the retrieved combination of algorithm and parameters to obtain a decoded object identifier. The logic device may then cause the camera 716 to read the object identifier and determine whether the object identifier and read identifier in fact match, or otherwise present a graphical representation on the display 711 for a user to make this determination.

Accordingly the invention may be embodied in the form of a computer program.

Furthermore, when suitably configured and connected, the elements of FIG. 7 may constitute a system for defining an identification code for an object. Such a system may be adapted to select a combination of an encoding algorithm and associated parameters from a memory (such as 702, 731, 732, 733 etc.) containing a plurality of a combination of encoding algorithm and parameters. The memory may further contain a respective encoding identifier associated with each combination. The system may further be adapted to define a URI having a hierarchical portion incorporating an identifier for said object encoded in accordance with said selected combination of algorithm and parameters, where the hierarchical portion further incorporates the encoding identifier corresponding to the selected combination of algorithm and parameters Such a system may further be adapted to encode the URI in a machine readable form.

Furthermore, when suitably configured and connected, the elements of FIG. 7 may constitute a system for verifying a URI containing an identification code for an object, adapted to extract an encoding identifier specifying a combination of algorithm and parameters from the URI; retrieving the combination of algorithm and parameters corresponding to said encoding identifier from a memory (such as 702, 731, 732, 733 etc.) containing a predefined plurality of combinations of encoding algorithm and parameters. The memory further contains a respective encoding identifier associated with each combination. The system may further be adapted to decode a remaining part of the URI using the retrieved combination of algorithm and parameters to obtain a decoded object identifier.

Such a system may further be adapted to prepare a representation of the decoded object identifier.

Such a system may further comprise a reader (such as elements 716, 715, 721 etc.) adapted to read a characteristic of the object reflecting the object identifier, and further be adapted to compare the characteristic with the representation of the decoded object identifier.

It will be appreciated that a "service", as used herein, is an application program executable across multiple user sessions. A service may be available to one or more system components, programs, and/or other services. In some implementations, a service may run on one or more server-computing devices.

When included, display subsystem 711 may be used to present a visual representation of data held by storage device. This visual representation may take the form of a graphical user interface (GUI). As the herein described methods and processes change the data held by the storage device 702, and thus transform the state of the storage device 702, the state of display subsystem 711 may likewise be transformed to visually represent changes in the underlying data. Display subsystem 711 may include one or more display devices utilizing virtually any type of technology. Such display devices may be combined with logic device and/or storage device in a shared enclosure, or such display devices may be peripheral display devices.

When included, input subsystem may comprise or interface with one or more user-input devices such as a keyboard 712, mouse 711, touch screen 711, or game controller (not shown). In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 720 may be configured to communicatively couple computing system with one or more other computing devices. For example, communication module of may communicatively couple computing device to remote service hosted for example on a remote server 76 via a network of any size including for example a personal area network, local area network, wide area network, or the internet. Communication subsystem may include wired and/or wireless communication devices compatible with one or more different communication protocols. As non-limiting examples, the communication subsystem may be configured for communication via a wireless telephone network 74, or a wired or wireless local- or wide-area network. In some embodiments, the communication subsystem may allow computing system to send and/or receive messages to and/or from other devices via a network such as the Internet 75. The communications subsystem may additionally support short range inductive communications 721 with passive devices (NFC, RFID etc).

Figure 8:
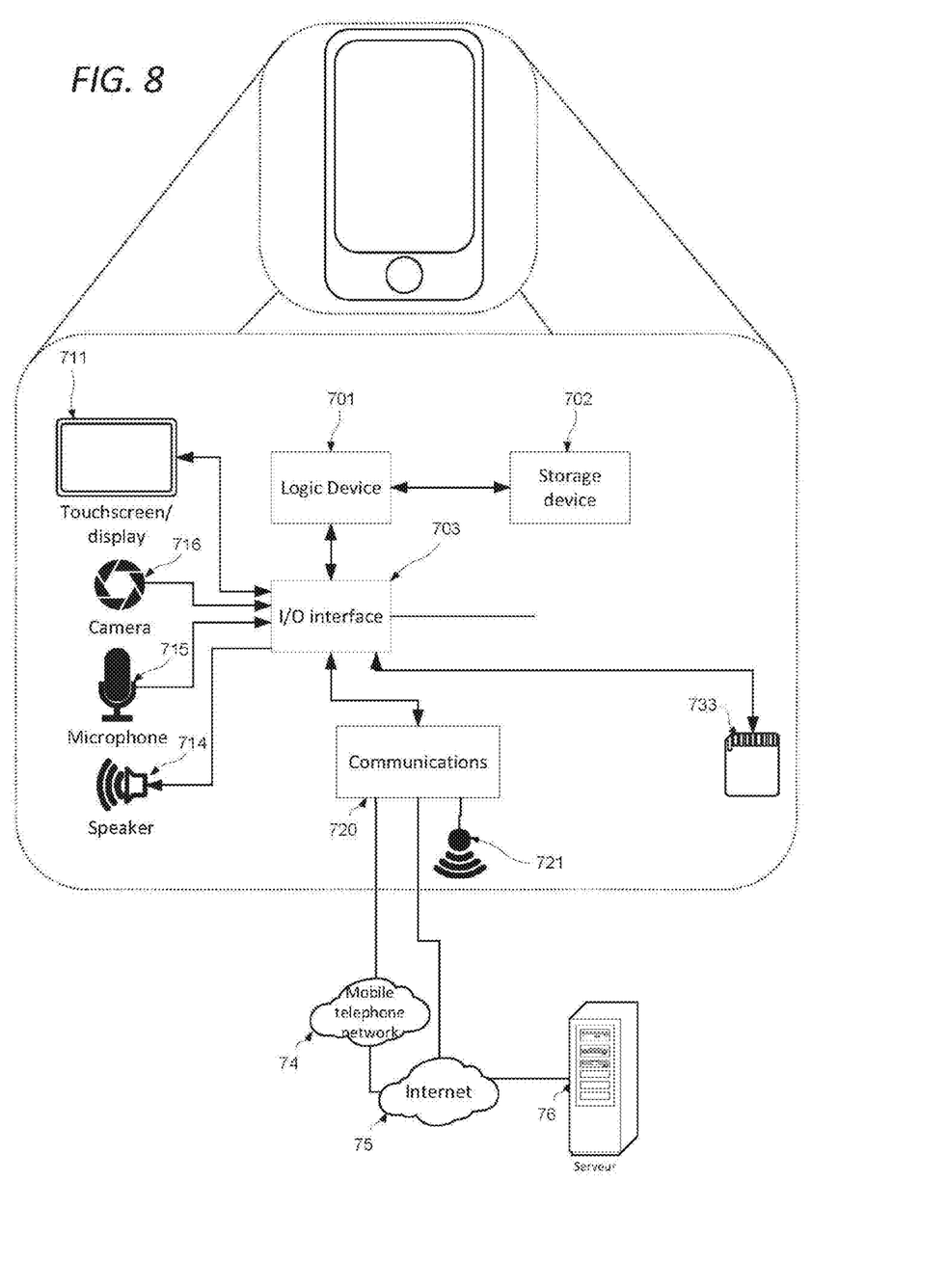
FIG. 8 shows a smartphone device adaptable to constitute an embodiment.
Figure 9:
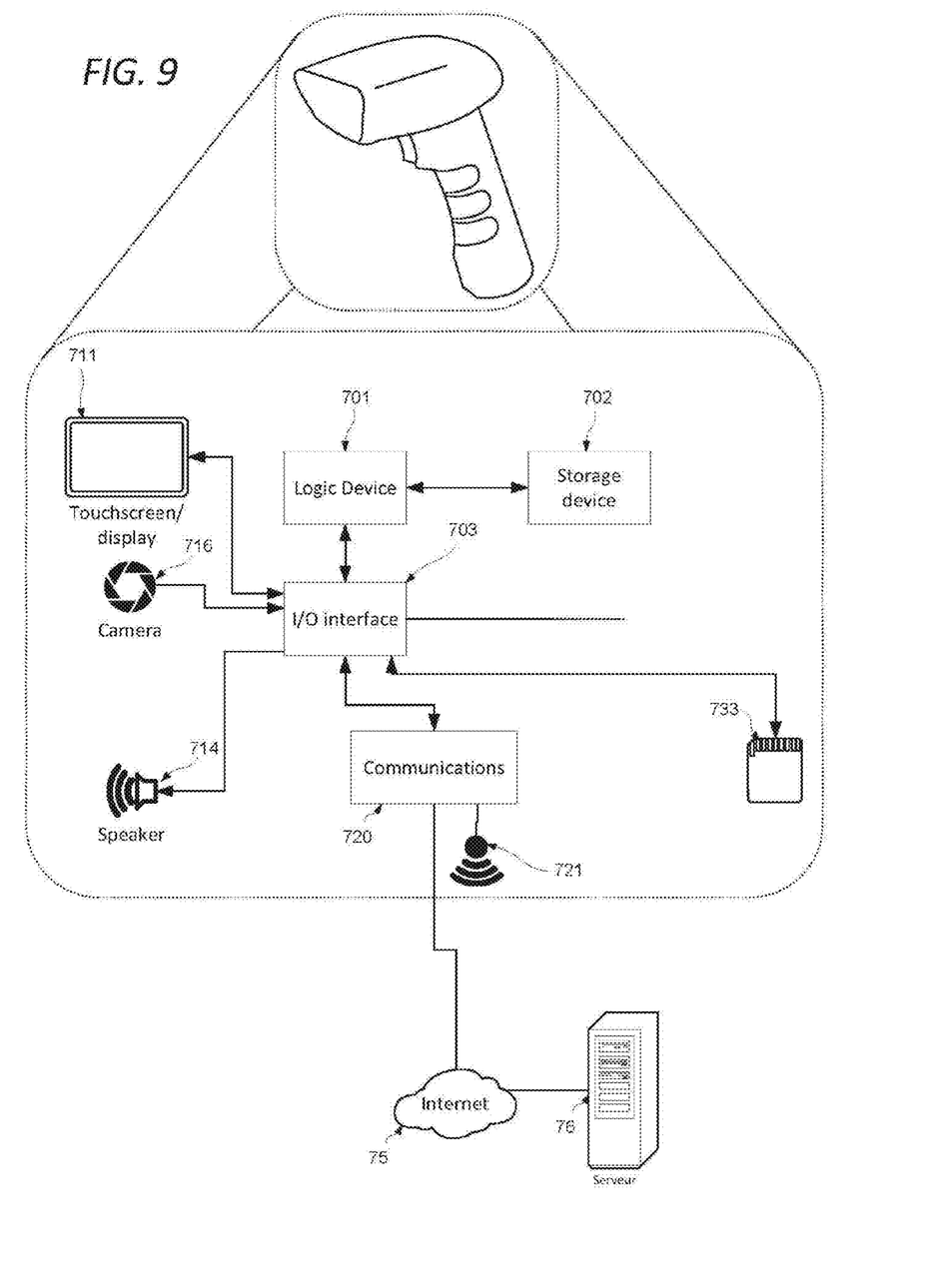
FIG. 9 shows a hand scanner device adaptable to constitute an embodiment.
Figure 10:
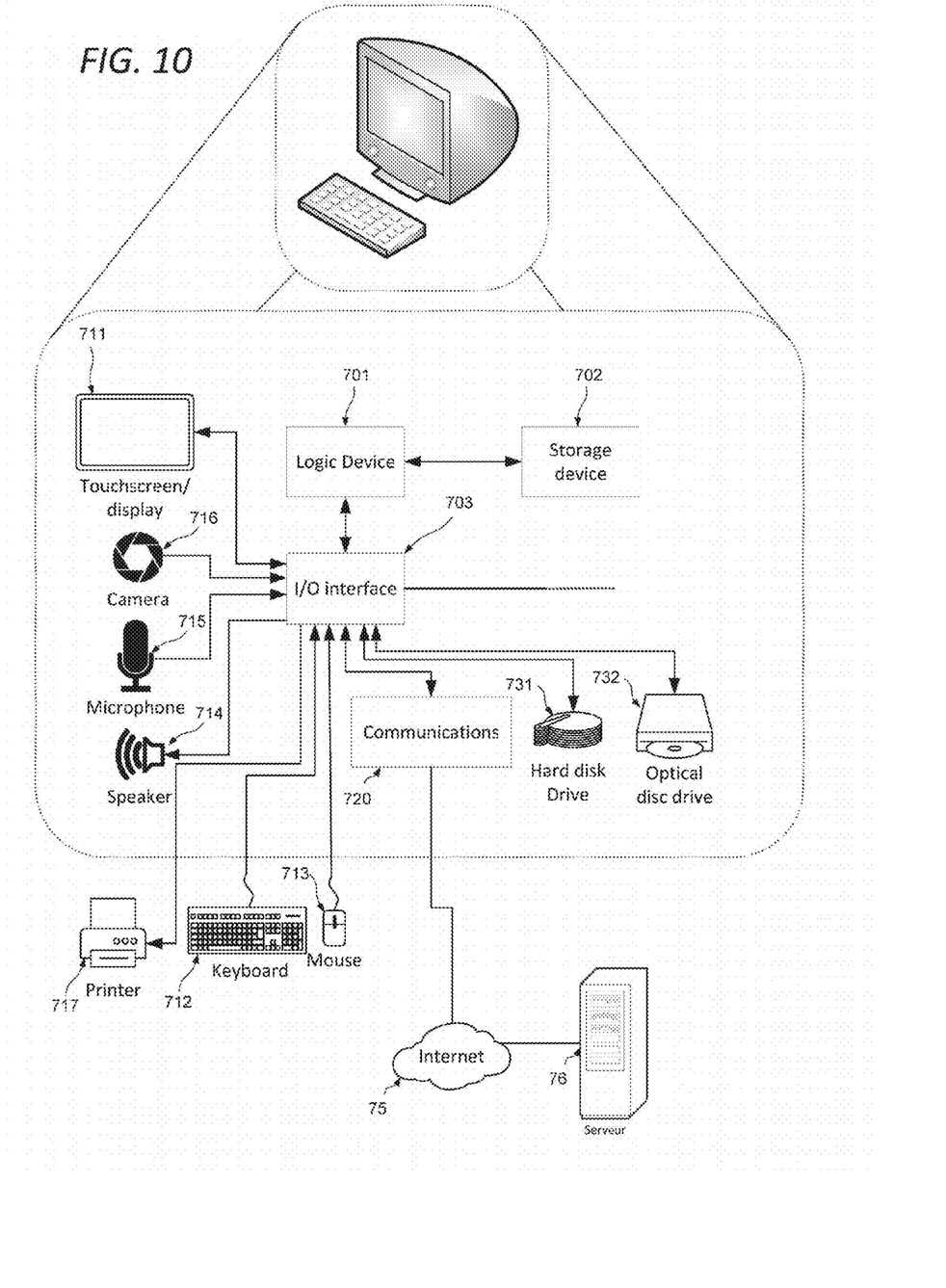
FIG. 10 shows a desktop computer device adaptable to constitute an embodiment.

The system of FIG. 7 is intended to reflect a broad range of different types of information handling system. It will be appreciated that many of the subsystems and features described with respect to FIG. 7 are not required for implementation of the invention, but are included to reflect possible systems in accordance with the present invention. It will be appreciated that system architectures vary widely, and the relationship between the different sub-systems of FIG. 7 is merely schematic, and is likely to vary in terms of layout and the distribution of roles in systems. It will be appreciated that, in practice, systems are likely to incorporate different subsets of the various features and subsystems described with respect to FIG. 7. FIGS. 8, 9 and 10 disclose further example devices in accordance with the present invention. Those of ordinary skill in the art will appreciate that systems may be employed in the future which also operate in accordance with the present invention.

FIG. 8 shows a smartphone device adaptable to constitute an embodiment. As shown in FIG. 8, the smartphone device incorporates elements 701, 702, 703, 720, 733, 714, 715, 716, 711 as described above. It is in communication with the telephone network 74 and a server 76 via the network 75. On the other hand, elements 731, 732, 717, 712, 713 are omitted. The features disclosed in this figure may also be included within a tablet device as well.

FIG. 9 shows a hand scanner device adaptable to constitute an embodiment. As shown in FIG. 9, the hand scanner device incorporates elements 701, 702, 703, 720, 733, 714 and 721 as described above. It is in communication with a server 76 via the network 75. On the other hand, elements 731, 732, 721, 716, 717, 712, 713 and 74 are omitted. 721 is present on the basis that the device shown is an NFC scanner, however this could of course be replaced with any sensor corresponding to any of the machine readable code types envisages herein.

FIG. 10 shows a computer device adaptable to constitute an embodiment. As shown in FIG. 10, the computer device incorporates elements 701, 702, 703, 720, 730, 732, 714, 715, 716 as described above. It is in communication with elements 717, 712 and 713 as peripheral devices which may also be incorporated in the same computer device, and with a server 76 via the network 75. On the other hand, elements 733, 721 and 74 are omitted, and element 711 is an ordinary display with or without touchscreen functionality.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An object associated with an object identifier and having a readable characteristic reflecting said object identifier and bearing a machine readable code, wherein said machine readable code comprises a Universal Resource Identifier (URI) having a hierarchical portion incorporating a representation of said object identifier encoded according to a selected one of a plurality of predefined combinations of encoding algorithms and parameters, each said combination having a respective encoding identifier, and wherein said hierarchical portion of said Universal Resource Identifier (URI) further specifies the encoding identifier corresponding to the combination of algorithm and parameters used to encode said object identifier.

2. The object of claim 1 wherein the scheme name portion of said Universal Resource Identifier (URI) is selected so as to cause said Universal Resource Identifier (URI) to be interpreted as a call to a local resource adapted to de-code said object identifier.

3. The object of claim 1 wherein the Universal Resource Identifier (URI) is defined so as to resolve to a web site.

4. The object of claim 1 in which said readable characteristic is a physical characteristic of said object.

5. The object of claim 4 in which said physical characteristic comprises a one or two dimensional image disposed on said object.

6. The object of claim 4 in which said physical characteristic comprises a surface bearing tactile or palpable features.

7. A method of defining an identification code for an object,
said method comprising the steps of:
selecting an object identifier for said object;
deriving a numerical representation of said object identifier;
selecting a combination of encoding algorithm and parameters from a predefined plurality of combinations of encoding algorithm and parameters, each said combination having a respective encoding identifier,
encoding said object identifier with said selected combination of encoding algorithm and parameters,
defining a Universal Resource Identifier (URI) having a hierarchical portion incorporating said encoded object identifier and the encoding identifier corresponding to the combination of algorithm and parameters used to encode said object identifier; and
encoding said Universal Resource Identifier (URI) in a machine readable form.

8. A method of verifying a Universal Resource Identifier (URI) containing an identification code for an object, said method comprising the steps of:
reading said Universal Resource Identifier (URI) via a machine reading interface;
extracting an encoding identifier specifying a combination of algorithm and parameters from said Universal Resource Identifier (URI);
retrieving the combination of algorithm and parameters corresponding to said encoding identifier from a predefined plurality of combinations of encoding algorithm and parameters, each said combination having a respective encoding identifier,
decoding a remaining part of said Universal Resource Identifier (URI) using the retrieved combination of algorithm and parameters to obtain a decoded object identifier; and
preparing a representation of said decoded object identifier.

9. The method of claim 8 comprising the further steps of reading a characteristic of said object, said characteristic reflecting said object identifier, and comparing said characteristic with said representation of said decoded object identifier.

10. The method of claim 9 comprising the further step prior to said step of extracting an encoding identifier, said further step comprising extracting the scheme name portion of said Universal Resource Identifier (URI), and interpreting the contents of the scheme name portion of the Universal Resource Identifier (URI) as a call to a local resource, wherein the remaining steps of the method are implemented by said resource.

11. The method of claim 8 comprising the further step of notifying the result of said verification to a user.

12. An apparatus for defining an identification code for an object, said apparatus adapted to select a combination of encoding algorithm and parameters from a memory containing a plurality of combinations of encoding algorithm and parameters, said memory further containing a respective encoding identifier associated with each said combination, said apparatus further adapted to define a Universal Resource Identifier (URI) having a hierarchical portion incorporating an identifier for said object encoded in accordance with said selected combination of algorithm and parameters, said hierarchical portion further incorporating the encoding identifier corresponding to said selected combination of algorithm and parameters.

13. The apparatus of claim 12 further adapted to encode said Universal Resource Identifier (URI) in a machine readable form.

14. An apparatus for verifying a Universal Resource Identifier (URI) containing an identification code for an object, said apparatus adapted to extract an encoding identifier specifying a combination of algorithm and parameters from said Universal Resource Identifier (URI); retrieve the combination of algorithm and parameters corresponding to said encoding identifier from a memory containing a predefined plurality of combinations of encoding algorithm and parameters, said memory further containing a respective encoding identifier associated with each said combination, said apparatus further adapted to decode a remaining part of said Universal Resource Identifier (URI) using the retrieved combination of algorithm and parameters to obtain a decoded object identifier.

15. The apparatus of claim 14 further adapted to prepare a representation of said decoded object identifier.

16. The apparatus of claim 15 further comprising reader adapted to read a characteristic of said object, said characteristic reflecting said object identifier, said apparatus further being adapted to comparing said characteristic with said representation of said decoded object identifier.

17. A computer program product stored in a non-transitory computer-readable storage medium for verifying a Universal Resource Identifier (URI) containing an identification code for an object, comprising computer-executable instructions for:
reading said Universal Resource Identifier (URI) via a machine reading interface;
extracting an encoding identifier specifying a combination of algorithm and parameters from said Universal Resource Identifier (URI);
retrieving the combination of algorithm and parameters corresponding to said encoding identifier from a predefined plurality of combinations of encoding algorithm and parameters, each said combination having a respective encoding identifier,
decoding a remaining part of said Universal Resource Identifier (URI) using the retrieved combination of algorithm and parameters to obtain a decoded object identifier; and
preparing a representation of said decoded object identifier.

* * * * *